United States Patent [19]
Lundberg

[11] Patent Number: 6,132,770
[45] Date of Patent: Oct. 17, 2000

[54] MULTIPLE UNIT EFFERVESCENT DOSAGE FORMS COMPRISING PROTON PUMP INHIBITOR

[75] Inventor: Per Johan Lundberg, Mölndal, Sweden

[73] Assignee: AstraZeneca AB, Sodertalje, Sweden

[21] Appl. No.: 08/793,077

[22] PCT Filed: Dec. 20, 1996

[86] PCT No.: PCT/SE96/01738

§ 371 Date: Feb. 13, 1997

§ 102(e) Date: Feb. 13, 1997

[87] PCT Pub. No.: WO97/25030

PCT Pub. Date: Jul. 17, 1997

[30] Foreign Application Priority Data

Jan. 8, 1996 [SE] Sweden ................................ 9600073

[51] Int. Cl.⁷ ................................ A61K 9/22; A61K 9/46
[52] U.S. Cl. ..................... 424/466; 424/465; 424/468; 424/470
[58] Field of Search ................... 424/464, 465, 424/480, 482, 466, 468, 470, 471, 494, 497

[56] References Cited

U.S. PATENT DOCUMENTS

| | | | |
|---|---|---|---|
| 4,289,751 | 9/1981 | Windheuser | 424/35 |
| 4,786,505 | 11/1988 | Lovgren et al. | 424/468 |
| 4,853,230 | 8/1989 | Lovgren et al. | 424/466 |
| 5,753,265 | 5/1998 | Bergstarnd et al. | 424/474 |
| 5,817,338 | 10/1998 | Bergstrand et al. | 424/468 |
| 5,824,339 | 10/1998 | Shimizu et al. | 424/466 |
| 5,840,737 | 11/1998 | Phillips | 514/338 |

FOREIGN PATENT DOCUMENTS

| | | |
|---|---|---|
| 0008780 | 8/1979 | European Pat. Off. . |
| 0072021 | 8/1982 | European Pat. Off. . |
| 0080341 | 11/1982 | European Pat. Off. . |
| 0108295 | 10/1983 | European Pat. Off. . |
| 0108504 | 10/1983 | European Pat. Off. . |
| 0111103 | 10/1983 | European Pat. Off. . |
| 0170752 | 12/1984 | European Pat. Off. . |
| 0223853 | 8/1987 | European Pat. Off. . |
| 0313328 | 4/1989 | European Pat. Off. . |
| 0342522 | 11/1989 | European Pat. Off. ......... A61K 9/20 |
| 0013566 | 1/1990 | European Pat. Off. . |
| 0391518 | 2/1990 | European Pat. Off. . |
| 0541369 | 11/1992 | European Pat. Off. . |
| 0587220 | 8/1993 | European Pat. Off. . |
| 0648487 | 10/1994 | European Pat. Off. . |
| 9317902 | 2/1996 | Rep. of Korea . |
| 94 3190 | 2/1996 | Rep. of Korea . |
| 2066070 | 12/1980 | United Kingdom . |
| 2091097 | 11/1981 | United Kingdom . |
| 2132887 | 11/1983 | United Kingdom . |
| 2219940 | 12/1989 | United Kingdom . |
| 2285989 | 1/1995 | United Kingdom . |
| 8501207 | 9/1984 | WIPO . |
| 8503436 | 2/1985 | WIPO . |
| 8702240 | 9/1986 | WIPO . |
| 9312772 | 12/1992 | WIPO . |
| 9403160 | 7/1993 | WIPO . |
| 9421239 | 9/1994 | WIPO . |
| 9510264 | 4/1995 | WIPO . |
| 9725030 | 7/1997 | WIPO . |

OTHER PUBLICATIONS

Lehmann et al. (1994) "Fast disintegrating controlled release tablets from coated particles" Drugs made in Germany 37:53–60.

Wan, L.S.C., "A Multiple–unit Tablet Formulation for Multi–layer Drug–coated Granules", S.T.P. Pharma Sciences, 4(5) (1994), pp. 336–342.

Primary Examiner—James M. Spear
Attorney, Agent, or Firm—White & Case LLP

[57] ABSTRACT

A new tableted multiple unit effervescent dosage form containing an acid susceptible proton pump inhibitor in the form of the racemate, an alkaline salt thereof or one of its single enantiomers or an alkaline salt thereof, and effervescent tablet constituents. The proton pump inhibitor is preferably omeprazole or an alkaline salt thereof, or S-omeprazole or an alkaline salt thereof. Further the invention refers to a method for the manufacture of such a formulation, and the use of such a formulation in medicine.

27 Claims, No Drawings

MULTIPLE UNIT EFFERVESCENT DOSAGE FORMS COMPRISING PROTON PUMP INHIBITOR

This application is a 371 of PCT/SE96/01738 filed Dec. 20, 1996.

FIELD OF THE INVENTION

The present invention is related to new pharmaceutical preparations in the form of a tableted multiple unit effervescent dosage form comprising an active substance in the form of an acid susceptible proton pump inhibitor, i.e. acid labile $H^+K^+$ ATPase inhibitors. The novel tableted dosage form is intended for oral use. Furthermore, the present invention refers to a method for the manufacture of such preparations and, to the use of such preparations in medicine.

BACKGROUND OF THE INVENTION

Acid labile $H^+K^+$ ATPase inhibitors also named as proton pump inhibitors are for instance compounds known under the generic names omeprazole, lansoprazole, pantoprazole, pariprazole, leminoprazole and others.

These active substances are useful for inhibiting gastric acid secretion in mammals and especially in man. In a more general sense, they may be used for prevention and treatment of gastric-acid related diseases in mammals and especially in man, including e.g. reflux oesophagitis, gastritis, duodenitis, gastric ulcer and duodenal ulcer. Furthermore, they may be used for treatment of other gastrointestinal disorders where gastric acid inhibitory effect is desirable e.g. in patients on NSAID therapy, in patients with Non Ulcer Dyspepsia, in patients with symptomatic gastro oesophageal reflux disease, and in patients with gastrinomas. They may also be used in patients in intensive care situations, in patients with acute upper gastrointestinal bleeding, pre- and postoperatively to prevent aspiration of gastric acid and to prevent and treat stress ulceration. Further, they may be useful in the treatment of psoriasis as well as in the treatment of Helicobacter infections and diseases related to these.

The active compounds are, however, susceptible to degradation/transformation in acidic reacting and neutral media. The degradation is catalyzed by acidic reacting compounds. The active compounds are stabilized with alkaline reacting compounds. Thus, the active substance being a proton pump inhibitor is best protected by an enteric coating layer. There are different enteric coating layered preparations of omeprazole as well as other proton pump inhibitors described in the prior art, see for example U.S. Pat. No. 4,786,505 (AB Hässle).

There has been a demand for a formulation with a rapid dissolution and a quick onset of action, furthermore a formulation which is pleasant to take for the patient and also which is suitable for patients with swallowing difficulties (dysphagia). There are a number of dosage forms that hold a good deal of promise in administering proton pump inhibitors. However, it has been difficult to find a vehicle which can satisfy all of many and some times conflicting needs and desires for such a dosage form.

One possible vehicle for administration of these active agents is effervescent tablets. Effervescence provides generally some measure of taste-masking. Prior to being taken by the patient, an effervescent composition is dissolved and/or dispersed in for example an aqueous medium, such as drinking water. Dissolution and/or dispersion takes place rapidly, with effervescence to give an agreeable presentation of the drug, particularly for patients who do not like tablets or find difficulty in swallowing tablets.

Effervescent compositions usually contain, in addition to the active ingredient, a source of carbon dioxide (such as an alkaline carbonate or bicarbonate) and an acid (such as for instance citric acid). The use of an acid in effervescent compositions in which the active ingredient is an acid labile substance such as an acid susceptible proton pump inhibitor presents a problem due to the instability of the proton pump inhibitor in the presence of acid.

Replacement of citric acid by monosodium citrate still fails to give a satisfactory level of stability of an acid labile histamine $H_2$-antagonist, whilst replacement of citric acid by disodium citrate results in insufficient effervescence and a prolonged dissolution time. EP 233853 proposes a mixture of monosodium citrate and disodium citrate as a solution to the problem. GB 2 219 940 A, proposes replacement of citric acid or the mixture of citrates proposed in EP 233853 by a monoalkalimetal citrate (monosodium citrate).

Effervescent tablets containing acid-sensitive agents have been manufactured by coating the acidic particles in the acid-base couple with a coating of a base to separate the pharmaceutically active substance, i.e. the acid-sensitive agent, from the acid of the effervescence, see for instance WO 94 21,239. The proposed solution results in that the active drug comes into contact with the resulting buffer when dissolving the tablet. Thus, the active drug must be stable in that buffer at the given pH. Furthermore, if the active drug has a bad taste, there will be problems to mask it. (For instance, omeprazole is such a compound that has a strongly bitter taste).

Another way to make effervescent tablets containing acid-labile drugs, such as erythromycine, has been proposed as described in U.S. Pat. No. 4,289,751. The active substance is incorporated in the effervescent tablet, in intimate contact with the effervescing acid-base couple. The effervescent tablet is then coated with an enteric coating polyrner. The aim of the preparation is that the tablet will be protected from the strongly acidic environment in the stomach by the enteric coating layer during the passage thereof. In the small intestines, the enteric coating layer is dissolved and the effervescent effect takes place in the intestines. One drawback with such a dosage form is that patients can experience problems due to the carbon dioxide liberated inside the gastrointestinal channel. Another drawback is varying residence time in the stomach before the tablet can arrive to an environment where the active substance can be dissolved, absorbed and can exert its effect Korean pat. appl. No. 93-17902 proposes another composition comprising an enteric coated tablet with an effervescent mixture layer inside the enteric coating. Also Korean pat. appl. No. 94-3190 describes a formulation of omeprazole with an effervescent mixture inside the enteric coating.

A way to circumvent the problems associated with the composition proposed in U.S. Pat. No. 4,289,751, i.e. with carbon dioxide created inside the gastrointestinal channel etc., and to avoid direct contact between the pharmaceutically active substance, i.e. the acid-labile compound, and acidic substances of the effervescence, and further to avoid direct contact of the active substance with a solution buffered to unsuitable pH, would be to use the active substance in the form of small enteric coating layered units comprising the pharmaceutically active substance. Such units are coating layered with a polymeric layer not dissolving in the solution formed when the effervescent tablet is dissolved.

These small coating layered units are taste-masked as they maintain their coating layer intact during and after intake of the effervescent dispersion and during passage of the stomach. The coating layer starts to dissolve upon arrival at the appropriate place in the gastrointestinal channel, i.e. in the small intestines (duodenum). The present invention now surprisingly provides such enteric coating layered units suitable for an effervescent formulation.

Preparation of a multiple unit tableted dosage form arises specific problems when enteric coating layered pellets containing acid susceptible proton pump inhibitors as active substances are compressed into tablets. If the enteric coating layer does not withstand the compression of the pellets into a tablet the susceptible active substance will be destroyed both by the acidic solution/dispersion formed upon effervescence or by penetrating acidic gastric juice upon administration, i.e. the acid resistance of the enteric coating layer of the pellets will not be sufficient in the tablet after compression.

SUMMARY OF THE INVENTION

The Applicant has now surprisingly found that effervescent tablets according to the present invention comprising enteric coated units of an acidic susceptible proton pump inhibitor can be manufactured by compressing said units into tablets without significantly affecting the properties of the enteric coating. As explained above, if the enteric coating is damaged during compression of the enteric coated units the acid resistance of said enteric coating in the manufactured tablets will not be sufficient and the manufactured tablets will not fulfil standard requirements on enteric coated articles, such as those defined in the United States Pharmacopeia USP. Furthermore, the active substance may be destroyed by the acidic solution/dispersion obtained by the effervescence, if such requirements not are fulfilled.

One object of the present invention is to provide a tableted multiple unit effervescent dosage form comprising an acid susceptible proton pump inhibitor, or an alkaline salt thereof or one of its single enantiomers or an alkaline salt thereof, in which the active substance is in the form of enteric coating layered units compressed together with effervescent tablet excipients into such an effervescent tablet. The enteric coating layer(s) covering the individual units of active substance has properties such that the compression of the units into a tablet does not significantly affect the acid resistance of the enteric coated units. The active substance is prevented from degradation and dissolution in acidic media and the dosage form has a good stability during long-term storage. The enteric coating covering the individual units disintegrates/dissolves rapidly in near neutral or alkaline media.

The tableted multiple unit effervescent dosage form is especially suitable for patients with swallowing disorders and in pediatrics.

DETAILED DESCRIPTION OF THE INVENTION

The novel tableted multiple unit effervescent dosage form comprising an active substance in the form of an acid susceptible proton pump inhibitor, or an alkaline salt thereof or one of its single enantiomers, or an alkaline salt thereof is characterized in the following way.

An effervescent tablet is compressed from a mixture of enteric coated layered pellets comprising the active substance and effervescent tablet constituents, and optionally other tablet excipients. Dissolution of the tablet in water gives such a pH value that the enteric coating layer of the pellets will not dissolve, i.e. a pH value normally less then 5.5, but depending on the specific enteric coating material used. Furthermore, the formulation is characterized in that the tablet per se is rapidly dissolving, and that it may contain taste improving agents, colourants, technical additives such as lubricating agents, disintegrants and wetting agents, and other tablet excipients.

The enteric coating layered units containing active substance and optionally alkaline reacting substances, are mixed with effervescent tablet constituents and optionally other excipients. The mixture is compressed into a tableted multiple unit effervescent dosage form. With the expression "units" is meant small beads, particles, granules or pellets, in the following referred to as pellets. All of or parts of the effervescent constituents may be granulated before compression or directly compressed together with the enteric coating layered units.

The compaction process (compression) for formulating the tableted multiple unit effervescent dosage form must not significantly affect the acid resistance of the enteric coating layered pellets. In other words the mechanical properties, such as the flexibility and hardness as well as the thickness, of the enteric coating layer(s) must secure that the requirements on enteric coated articles in the United States Pharmacopeia USP are accomplished and the acid resistance does not decrease more than 10% during the compression of pellets into tablets.

The acid resistance is defined as the amount of active substance in tablets or pellets after being exposed to simulated gastric fluid, USP, or to 0.1 M HCl(aq) relative to that of unexposed tablets or pellets, respectively. The test is accomplished in the following way. Tablets or pellets are exposed to simulated gastric fluid at a temperature of 37° C. The tablets disintegrate and release the enteric coated pellets to the medium. After two hours the enteric coated pellets are removed and analyzed for active substance content using High Performance Liquid Cromatography (HPLC).

Active Substances

The proton pump inhibitors are for example compounds of the general formula I

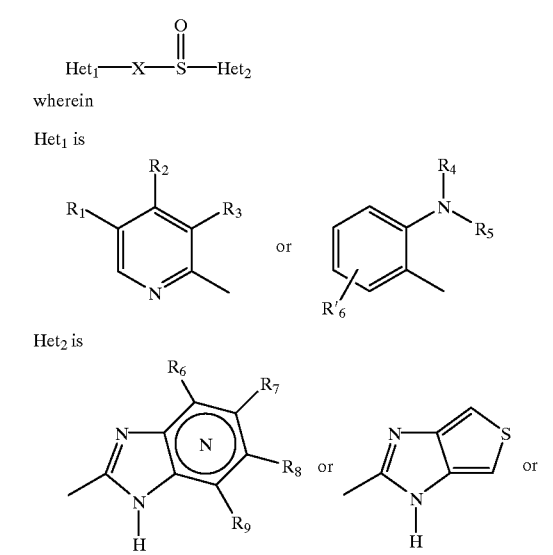

-continued

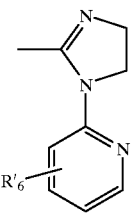

X =

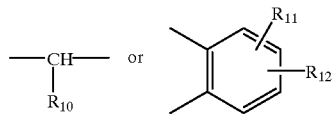

wherein

N in the benzimidazole moiety means that one of the carbon atoms substituted by $R_6$–$R_9$ optionally may be exchanged for a nitrogen atom without any substituents;

$R_1$, $R_2$ and $R_3$ are the same or different and selected from hydrogen, alkyl, alkoxy optionally substituted by fluorine, alkylthio, alkoxyalkoxy, dialkylamino, piperidino, morpholino, halogen, phenyl and phenylalkoxy;

$R_4$ and $R_5$ are the same or different and selected from hydrogen, alkyl and aralkyl;

$R'_6$ is hydrogen, halogen, trifluoromethyl, alkyl and alkoxy;

$R_6$–$R_9$ are the same or different and selected from hydrogen, alkyl, alkoxy, halogen, haloalkoxy, alkylcarbonyl, alkoxycarbonyl, oxazolyl, trifluoroalkyl, or adjacent groups $R_6$–$R_9$ form ring structures which may be further substituted;

$R_{10}$ is hydrogen or forms an alkylene chain together with $R_3$ and $R_{11}$ and $R_{12}$ are the same or different and selected from hydrogen, halogen or alkyl and alkyl groups, alkoxy groups and moities thereof may be branched and straight $C_1$–$C_9$-chains or comprise cyclic alkyl groups, for example cycloalkylalkyl.

Examples of proton pump inhibitors according to formula I are

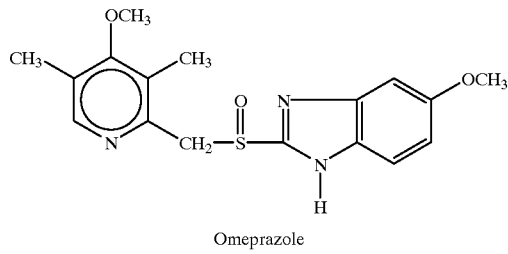

Omeprazole

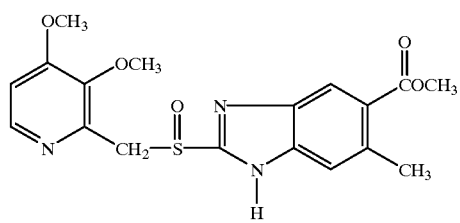

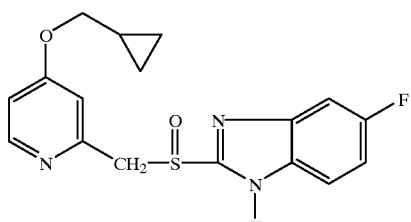

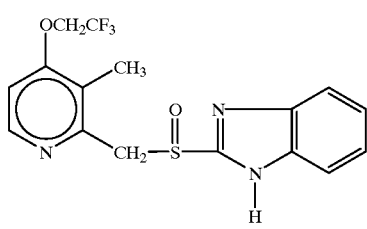

Lansoprazole

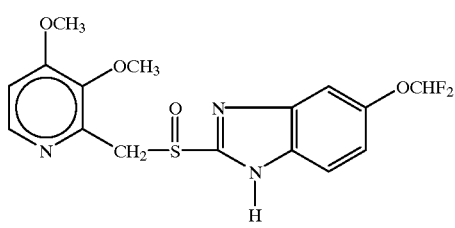

Pantoprazole

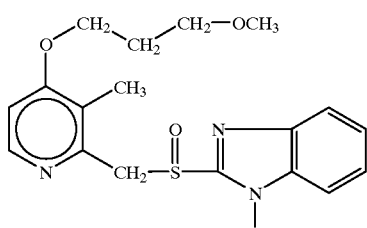

Pariprazole

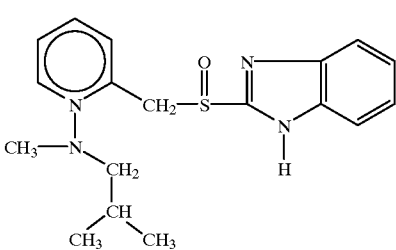

Leminoprazole

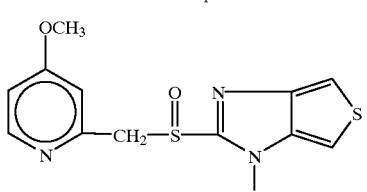

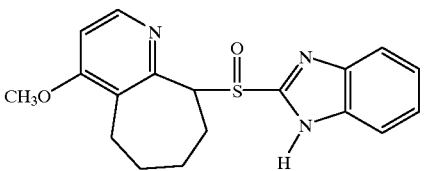

-continued

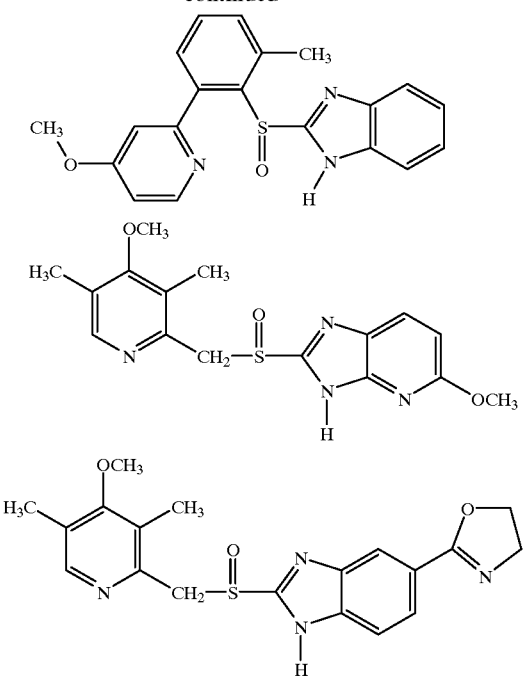

The proton pump inhibitors used in the dosage forms of the invention may be used in neutral form or in the form of an alkaline salt, such as for instance the $Mg^{2+}, Ca^{2+}, Na^+, K^+$ or $Li^+$ salts, preferably the $Mg^{2+}$ salts. Further where applicable, the compounds listed above may be used in racemic form or in the form of a substantially pure enantiomer thereof, or alkaline salts of the single enantiomers.

Suitable proton pump inhibitors are for example disclosed in EP-A1-0005129, EP-A1-174 726, EP-A1-166 287, GB 2 163 747 and WO90/06925, WO91/19711, WO91/19712, and further especially suitable compounds are described in WO95/01977 and WO94/27988.

The effervescent tablet constituents used in the tableted dosage form according to the present invention must not interfere in a disadvantagely manner with the active substance in the prepared tablet. Thus, the buffering components in the effervescent system should, dissolved in water, result in a solution with a pH value that is below the pKa of the enteric coating polymer used on the individually enteric coating layered units comprising the acid susceptible proton pump inhibitor. In most cases the pH value of the obtained solution/dispersion formed upon effervescence should be below 5.5, but depends on the specific enteric coating polymer used. The pH is important to ensure that the enteric coating layer of the units remain intact during the administration to protect the acid susceptible proton pump inhibitor during passage of the stomach, and later disintegrate/dissolve in the small intestine where dissolution of the active substance is desired.

The buffering components of the effervescent constituents can generally be divided in two categories; a carbon dioxide source and an acidic component. The latter reacts with the carbon dioxide source resulting in the development of carbon dioxide gas. The effervescent constituents may also include other tableting excipients such as for instance binding agents, diluents, lubricants, disintegrating agents, surfactants, taste improving agents, colorants or the like.

As carbon dioxide source can be used for instance alkali metal carbonates or bicarbonates, alkaline earth metal carbonates or bicarbonates, or other inorganic salts containing carbonate or bicarbonate ions.

Acidic components suitable to incorporate in an effervescent tablet are preferably solid acidic compounds and include for instance monosodium dihydrogen phosphate, or tartaric acid, citric acid and other weak organic acids.

Further components used in the preparation according to the present invention are described more in detail below.

Core Material—Containing an Acid Susceptible Proton Pump Inhibitor.

The core material for the individually enteric coated pellets can be constituted according to different principles. Inert seeds layered with active substance, optionally mixed with alkaline reacting compounds, can be used as the core material for the further processing.

The seeds which are to be layered with the acid susceptible proton pump inhibitor can be water insoluble seeds comprising different oxides, celluloses, organic polymers and other materials, alone or in mixtures or water-soluble seeds comprising different inorganic salts, sugars, nonpareils and other materials, alone or in mixtures. Further, the seeds may comprise the proton pump inhibitor in the form of crystals, agglomerates, compacts etc. The size of the seeds is not essential for the present invention but may vary between approximately 0.1 and 2 mm. The seeds layered with the proton pump inhibitor are produced either by powder or solution/suspension layering using for instance granulation or spray coating layering equipment.

Before the seeds are layered the active substance may be mixed with further components. Such components can be binders, surfactants, fillers, disintegrating agents, alkaline reacting additives or other pharmaceutically acceptable ingredients, alone or in mixtures. The binders are for example polymers such as hydroxypropyl methylcellulose, hydroxypropyl cellulose and carboxymethylcellulose sodium, polyvinyl pyrrolidone, sugars, starches or other pharmaceutically acceptable substances with cohesive properties. Suitable surfactants are found in the groups of pharmaceutically acceptable non-ionic or ionic surfactants such as for instance sodium lauryl sulfate.

Alternatively, the core material can be prepared as substantially homogeneous cores containing omeprazole or one of its single enantiomers or an alkaline salt of omeprazole or one of its single enantiomers mixed with suitable constituents, optionally mixed with alkaline reacting compounds. Said core materials may be produced by extrusion/spheronization, balling or compression utilizing different process equipments.

The size of the formulated homogeneous core material is approximately between 0.1 and 4 mm and preferably between 0.1 and 2 mm. The manufactured homogeneous core materials can be further layered with additional ingredients comprising active substance and/or used for further processing.

The active substance is mixed with pharmaceutical constituents to obtain preferred handling and processing properties and a suitable concentration of active substance in the final mixture. Pharmaceutical constituents such as fillers, binders, lubricants, disintegrating agents, surfactants and other pharmaceutically acceptable additives, can be used.

The active substance may also be mixed with an alkaline reacting pharmaceutically acceptable substance (or substances). Such substances can be chosen among, but are not restricted to, substances such as the sodium, potassium, calcium, magnesium and aluminium salts of phosphoric acid, carbonic acid, citric acid or other suitable weak inorganic or organic acids; aluminium hydroxide/sodium bicarbonate coprecipitate; substances normally used in antacid preparations such as aluminium, calcium and magnesium hydroxides; magnesium oxide or composite substances, such as $Al_2O_3.6MgO.CO_2.12H_2O$, $(Mg_6Al_2(OH)_{16} CO_3.4H_2O)$, $MgO.Al_2O_3.2SiO_2.nH_2O$ or similar compounds; organic pH-buffering substances such as trihydroxymethylaninomethane, basic amino acids and their salts or other similar, pharmaceutically acceptable pH-buffering substances.

Alternatively, the aforementioned core material can be prepared by using spray drying or spray congealing technique.

The active substance is in the form of an acid labile $H^+K^+$ ATPase inhibitor according to formula I or an alkaline salt thereof or one of its single enantiomers. These compounds have an asymmetric centre in the sulfur atom, i.e. exists as two optical isomers (enantiomers). Both the pure enantiomers, racemic mixtures (50% of each enantiomer) and unequal mixtures of the two enantiomers are suitable for the pharmaceutical formulation according to the present invention.

Enteric Coating Layer(s)—for Enteric Coating Layering of the Core Material of a Proton Pump Inhibitor.

Before applying enteric coating layer(s) onto the core material in the form of individual pellets, said pellets may optionally be covered with one or more separating layers comprising pharmaceutical excipients optionally including pH-buffering, alkaline compounds. This/these separating layer(s) separate(s) the core material from the outer layer(s) being enteric coating layer(s). The separating layer(s) protecting the core material of a proton pump inhibitor should be water soluble or rapidly disintegrating in water.

The separating layer(s) can be applied on to the core material by coating or layering procedures in suitable equipments such as coating pan, coating granulator or in a fluidized bed apparatus using water and/or organic solvents for the coating process. As an alternative the separating layer(s) can be applied to the core material by using coating technique. The materials for separating layers are chosen among the pharmaceutically acceptable compounds such as, for instance, sugar, polyethylene glycol, polyvinylpyrrolidone, polyvinyl alcohol, polyvinyl acetate, hydroxypropyl cellulose, methylcellulose, ethylcellulose, hydroxypropyl methyl cellulose, carboxymethylcellulose sodium and others, used alone or in mixtures. Additives such as plasticizers, colorants, pigments, fillers, anti-tacking and anti-static agents, such as for instance magnesium stearate, titanium dioxide, talc and other additives may also be included into the separating layer(s).

When the optional separating layer(s) is applied to the core material it may constitute a variable thickness. The maximum thickness of the optional separating layer(s) is normally only limited by processing conditions. The separating layer(s) may serve as a diffusion barrier and may act as a pH-buffering zone. The pH-buffering properties of the separating layer(s) can be further strengthened by introducing into the layer(s) substances chosen from a group of compounds usually used in antacid formulations such as, for instance, magnesium oxide, hydroxide or carbonate, aluminium or calcium hydroxide, carbonate or silicate; composite aluminium/magnesium compounds such as, for instance $Al_2O_3.6MgO.CO_2.12H_2O$, $(Mg_6Al_2(OH)_{16} CO_3.4H_2O)$, $MgO.Al_2O_3.2SiO_2.nH_2O$, aluminium hydroxide/sodium bicarbonate coprecipitate or similar compounds; or other pharmaceutically acceptable pH-buffering compounds such as, for instance the sodium, potassium, calcium, magnesium and aluminium salts of phosphoric, carbonic, citric or other suitable, weak, inorganic or organic acids; or suitable organic bases, including basic amino acids and salts thereof. Talc or other compounds may be added to increase the thickness of the layer(s) and thereby strengthen the diffusion barrier. The optionally applied separating layer(s) is not essential for the invention. However the separating layer(s) may improve physical and chemical properties of the novel multiple unit tableted dosage form.

Alternatively, the separating layer may be formed in situ by a reaction between an enteric coating polymer layer applied on the core material and an alkaline reacting compound in the core material. Thus, the separating layer formed comprises a water soluble salt formed between the enteric coating layer polymer(s) and an alkaline reacting compound which is in the position to form a salt.

One or more enteric coating layers are applied onto the core material or onto the core material covered with separating layer(s) by using a suitable coating technique. The enteric coating layer material may be dispersed or dissolved in either water or in suitable organic solvents. As enteric coating layer polymers one or more, separately or in combination, of the following can be used; e.g. solutions or dispersions of methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating layer polymer(s).

The enteric coating layers contain pharmaceutically acceptable plasticizers to obtain the desired mechanical properties, such as flexibility and hardness of the enteric coating layers. Such plasticizers are for instance, but not restricted to, cetanol, triacetin, citric acid esters, phthalic acid esters, dibutyl sebacate, polyethylene glycol, polysorbates or other plasticizers.

The amount of plasticizer is optimized for each enteric coating layer formula, in relation to selected enteric coating layer polymer(s), selected plasticizer(s) and the applied amount of said polymer(s), in such a way that the mechanical properties, i.e. flexibility and hardness of the enteric coating layer(s), for instance exemplified as Vickers hardness are adjusted so that the acid resistance of the pellets covered with enteric coating layer(s) does not decrease significantly during the compression of pellets into tablets. The amount of plasticizer is usually in the range of 1–50% by weight of the enteric coating layer polymer(s), preferably 10–50% and more preferably 15–50%. Additives such as dispersants, colorants, pigments, polymers e.g. poly (ethylacrylat, methylmethacrylat), anti-tacking and anti-foaming agents may also be included into the enteric coating layer(s). Other compounds may be added to increase film thickness and to decrease diffusion of acidic gastric juices into the acid susceptible material.

To protect an acid susceptible proton pump inhibitor and to obtain an acceptable acid resistance of the multiple unit tableted dosage form, according to the invention the enteric coating layer(s) constitutes a thickness of approximately at least 10 µm, preferably more than 20 µm. The maximum thickness of the applied enteric coating layer(s) is normally limited by processing conditions, and the desired dissolution profile.

Over-coating Layer

Pellets covered with enteric coating layer(s) may further be covered with one or more over-coating layer(s). This over-coating layer(s) should be water soluble or rapidly disintegrating in water. The over-coating layer(s) can be applied to the core material by coating or layering procedures in suitable equipments such as coating pan, coating granulator or in a fluidized bed apparatus using water and/or organic solvents for the coating process. The materials for over-coating layers are chosen among the pharmaceutically acceptable compounds such as, for instance sugar, polyethylene glycol, polyvinylpyrrolidone, polyvinyl alcohol, polyvinyl acetate, hydroxypropyl cellulose, methylcellulose, ethylcellulose, hydroxypropyl methyl cellulose, carboxymethylcellulose sodium and others, used alone or in mixtures. Additives such as plasticizers, colorants, pigments, fillers, anti-tacking and anti-static agents, such as for instance magnesium stearate, titanium dioxide, talc and other additives may also be included into the over-coating layer(s). Said over-coat may further prevent potential agglomeration of coated pellets, protect the enteric coating towards cracking during the compaction process and enhance compressability during tableting. The maximum thickness of the applied over-coating layer(s) is normally limited by processing conditions, and the desired dissolution profile. The above described over-coating layer may also be used as a tablet coating layer to obtain tablets of good appearance.

Effervescent Preparation

The effervescent constituents can be dry mixed, wet granulated, compacted, melt granulated or prepared according to any known granulation technique. When wet granulated the acidic component may be granulated separately or in combination with the carbon dioxide source. If granulated in combination, it is advantageous to use a granulation liquid that contains as little water as possible, e.g. ethanol 99%.

Effervescent Tablets

The enteric coating layered pellets comprising an acid susceptible proton pump inhibitor are mixed with effervescent constituents and optionally with tablet excipients such as fillers, binders, disintegrants, lubricants and other pharmaceutical acceptable additives and compressed into a multiple unit tableted dosage form according to the present invention. The proton pump inhibitor as well as the effervescent constituents are defined above.

By choosing small enteric coated pellets in the formulation according to the present invention, the fraction of pellets in each tablet can be held high and the pellets evenly distributed within the tablet and easily dispersible upon effervescence.

Thus, the formulation according to the invention consists of core material containing an active substance, optionally mixed with alkaline reacting compound(s), and tablet excipients. The addition of an alkaline reacting material may not be necessary, but such a substance may further enhance the stability of the active substance. The core material is optionally coated with one or more separating layer(s) optionally containing pH-buffering substance(s). The pellets, optionally covered with a separating layer(s), are then covered with one or more enteric coating(s) rendering the pellets being insoluble in acidic media, but disintegrating/dissolving in near neutral to alkaline media such as, for instance the liquids present in the proximal part of the small intestine where dissolution is desired. The enteric coating layered pellets may further be covered with an over-coat before formulated together with the effervescent constituents into the tableted multiple unit effervescent dosage form as mentioned above.

Process

The process for the manufacture of the dosage form represents a further aspect of the invention. The pharmaceutical processes can preferably be completely water-based and different ways to practice the invention are described in the accompanying examples below.

Use of Preparation

The preparation according to the invention is especially advantageous in reducing gastric acid secretion. It is administered one to several times a day, preferable once or twice daily. The typical daily dose of the active substance varies and will depend on various factors such as the individual requirements of the patients, the mode of administration and disease. In general the daily dose will be in the range of 1–1000 mg of active substance. Preferred dosages are 10–100 mg of the proton pump inhibitor.

The present invention is described in more detail by the following non-limiting example.

EXAMPLE 1

Effervescent tablets containing 20 mg omeprazole.

Manufacturing of pellets containing magnesium omeprazole.

| Core material | |
| --- | --- |
| Magnesium omeprazole | 12.00 kg |
| Non-pareil cores | 12.00 kg |
| Hydroxypropyl methylcellulose | 1.8 kg |
| Water purified | 35.4 kg |
| Separating layer | |
| Core material (acc. to above) | 23.50 kg |
| Hydroxypropyl cellulose | 2.35 kg |
| Talc | 4.03 kg |
| Magnesium Stearate | 0.34 kg |
| Water purified | 48.00 kg |
| Enteric coating layer | |
| Pellets with a sep layer (acc. to above) | 29.00 kg |
| Methacrylic acid copolymer (30% suspension) | 38.70 kg |
| Triethyl citrate | 3.48 kg |
| Mono- and diglycerides (NF) | 0.58 kg |
| Polysorbate 80 | 0.06 kg |
| Water purified | 22.68 kg |
| Over-coating layer | |
| Enteric coated pellets (acc. to above) | 44.7 kg |
| Hydroxypropyl methylcellulose | 0.58 kg |
| Mg-Stearate | 0.02 kg |
| Water purified | 11.6 kg |

Suspension layering was performed in a fluid bed apparatus. Magnesium omeprazole was sprayed onto inert suger seeds (non-pareil cores) from a water suspension containing the dissolved binder.

The prepared core material was coating layered with a separating layer in a fluid bed apparatus with a hydroxypropyl cellulose solution containing talc and magnesium stearate. The enteric coating layer consisting of methacrylic acid copolymer, mono- and diglycerides, triethylcitrate and polysorbate was sprayed onto the pellets (layered with a separating layer) in a fluid bed apparatus. In the same type of apparatus the enteric coating layered pellets were coated with hydroxypropyl methylcellulose/Mg-stearate suspension. The pellets covered by an over-coating layer were classified by sieving.

The obtained enteric coating layered pellets were mixed with prepared granules and other components as described below and thereafter compressed to effevescent tablets.

| Granulation (1000 tablets); | |
| --- | --- |
| Citric acid anhydrous | 605 g |
| Mannitol dried | 200 g |
| Riboflavine | 0.1 g |
| Polyvinylpyrrolidone K-25 (PVP K-25) | 6.0 g |
| EtOH 99% (w/v) | 90 g |

The PVP K-25 was dissolved in the ethanol to give the granulating solution. In this solution the riboflavine was dispersed. The citric acid and mannitol were mixed and the liquid was added and the mass further mixed. Then the mass was put on a tray and dried in a drying oven for approx. 2 hrs at 55 degrees Celsius. The granulate was milled to pass sieve 1.0 mm.

A pre-mix consisting of the following was prepared by dry mixing in a turbula mixer;

| | |
| --- | --- |
| Sodium carbonate anhydrous | 36 g |
| Sodium dodecyl sulphate | 1 g |
| Sodium stearylfumarate | 14 g |
| Essence orange | 2.0 g |
| Saccharine Sodium | 2.0 g |
| Polyvinyl pyrrolidone cross-linked | 70 g |
| Enteric coated pellets from above | 95.7 g |

Final mixing was performed in a Kenwood mixer where the following ingredients were dry mixed:

| | |
| --- | --- |
| Granulate from above | 811.1 g |
| Premix from above | 220.7 g |
| Sodium bicarbonate | 453 g |

The final mixing time was 4 minutes.

Compression to tablets was done on a tableting machine equipped with punches giving 20 mm diameter flat tablets with bevelled edges.

Tablet weight was 1485 mg. The compressed tablets had an average height of 3.6 mm (n=10). The effervescence time of the tablets wase measured by placing the tablet in a basket of metal wiring and then immersing the basket in 300 ml of water at 20 degrees Celsius. The effervescence time was considered finished when there was no material left in the immersed basket For this tablet composition the time was 30 seconds.

One tablet was placed in 100 ml purified water. The pH of the obtained dispersion was 4.8. Another tablet was exposed for 0.1 M HCl during 2 hours. The liberated enteric coated units were transferred to phosphate buffer solution of pH 6.8. After 30 min 91% of the omeprazole dose was found in the solution.

EXAMPLE 2

Preparation of enteric coating layered pellets containing lansoprazole.

| Core material | |
| --- | --- |
| Non-pareil cores | 400 g |
| Lansoprazole | 400 g |
| Hydroxypropyl methylcellulose | 80 g |
| Sodium laurylsulphate | 3 g |
| Water purified | 1360 g |
| Separating layer | |
| Core material (acc. to above) | 100 g |
| Hydroxypropyl methylcellulose | 9 g |
| Polyethyleneglycol 6000 | 1 g |
| Talc | 18 g |
| Ethanol 95% | 250 g |
| Water purified | 250 g |
| Enteric coating layer | |
| Sub-coated pellets (acc. to above) | 100 g |
| Hydroxypropyl methylcellulose phtalate | 40 g |
| Acetyltributyl citrate | 8 g |
| Cetanol | 2 g |
| Ethanol 95% | 162 g |
| Acetone | 378 g |

Suspension layering was performed in a Wurster equipped fluid bed apparatus. Lansoprazole was sprayed onto inert non-pareil cores from a water suspension containing lansoprazole, the dissolved binder and the wetting agent.

The prepared core material was coating layered with a separating layer in the same equipment by spraying a suspension of talc in a HPMC/PEG- solution. PEG was added to act as a plasticizer for the HPMC.

Enteric coating layer was applied in the same equipment by spraying the enteric coating polymer solution (including additives according to above) onto the pellets (layered with a separating layer). The obtained enteric coating layered pellets were mixed with prepared granules and other component as described in example 1, and compressed into effervescent tablets.

EXAMPLE 3

Effervescent tablets 20 mg containing 20 mg omeprazole

Manufacturing of pellets.

| Core material | |
| --- | --- |
| Suspension for layering | |
| Magnesium omeprazole | 5.0 kg |
| Hydroxypropyl methylcellulose | 0.8 kg |
| Water purified | 14.3 kg |
| Seeds for layering | |
| Non-pareil cores | 10.0 kg |

The active substance was suspended in a solution prepared of the hydroxypropyl methylcellulose in the water, and thereafter homogenized in a ball mill.

The suspension was sprayed onto the seeds in a Wurster equipped fluidized bed apparatus.

| Separating layer | |
| --- | --- |
| Core material (acc. to above) | 14.6 kg |
| Hydroxypropyl cellulose | 1.5 kg |
| Talc | 2.5 kg |
| Magnesium Stearate | 0.2 kg |
| Water purified | 29.2 kg |

The talc and magnesium stearate were suspended in a solution prepared by dissolving the hydroxypropyl cellulose in the water. The suspension was sprayed onto the core material in the same equipment as above.

| Enteric coating layer | |
| --- | --- |
| Prepared pellets (acc. to above) | 250 g |
| Methacrylic acid copolymer (30% suspension) | 458 g |
| Triethyl citrate | 41 g |
| Titanium dioxide | 19 g |
| Mono- and diglycerides (NF) | 7 g |
| Polysorbate 80 | 0.7 g |
| Water purified | 329 g |

The pH of the methacrylic acid copolymer coating suspension was first adjusted to 4.0 by adding 14 ml of 0.5 M sodium hydroxide solution. Thereafter all of the triethylcitrate was added. (=Suspension A.)

The polysorbate 80 was mixed with 120 g of water, whereafter the mono- and diglycerides was added and this mixture was heated to above 70° C. for 10 minutes and the cooled during agitation to room temperature. (=Emulsion B.)

The titanium dioxide was suspended in 120 g of water. The pH of the suspension was 4.4. (=Suspension C.)

The emulsion B, the suspension C and 89 g of water were added to suspension A. The pH of the mixture was checked and found to be 4.2.

(At pH below 4.5 this enteric coating suspension showed no signs of precipitation.)

The suspension (during agitation with a magnetic stirrer) was sprayed onto the core material in a Wurster equipped fluidized bed apparatus.

The obtained enteric coated pellets were mixed with powders and effervescent granules and thereafter compressed to effervescent tablets.

| Effervescent granules; | |
| --- | --- |
| Citric acid anhydrous | 11.4 kg |
| Sodium bicarbonate | 8.4 kg |
| Polyvinylpyrrolidone K-25 (PVP K-25) | 0.3 kg |
| EtOH 99% (w/v) | 0.8 kg |
| water purified | 0.3 kg |

The PVP K-25 was dissolved in the ethanol+water to give the granulating solution. This solution was used to granulate the citric acid sodium bicarbonate mixture. The wet mass was dried at 55° C., and after cooling to room temperature the granulate was milled to pass sieve 1.1 mm.

A pre-mix (for 400 tablets) was prepared by dry mixing in a Kenwood mixer the following;

| | |
| --- | --- |
| Sodium carbonate anhydrous | 38 g |
| Sorbitol | 160 g |
| Antifoam M | 5.8 g |

The premix was passed through a 0.5 mm sieve.

Final mixing (for 400 tablets) was performed in the same Kenwood mixer where the following ingredients were dry mixed:

| | |
| --- | --- |
| Effervescent granules from above | 909 g |
| Premix from above | 204 g |
| Sodium sterylfumarate (passing sieve 0.5 mm) | 7 g |
| Enteric coated pellets from above | 70 g |

Compression to tablets was done on a tableting machine equipped with punches giving 25 mm diameter flat tablets.

Tablet weight was 2970 mg. The compressed tablets had an average height of 4.3 mm (n=4) and an average hardness of 77 N (n=10). The effervescense time of the tablets was measured by putting the tablet in a basket of metal wiring and then immersing the basket in 150 ml of water (20 degrees Celsius). The effervescense time was considered finished when there was no material left in the immersed basket. For this tablet composition the time was 55 seconds.

The pH of the obtained dispersion testing in the tablet in 150 ml purified water was 5.0.

Gastric juice resistance (determined as % of the dose omeprazole remaining after exposure for 0.1 M HCl during 2 hours) was 91%.

EXAMPLE 4

Effervescent tablets containing 40 mg omeprazole.
Manufacturing of pellets.

| Core material | |
| --- | --- |
| Suspension for layering | |
| Magnesium omeprazole | 5.5 kg |
| Hydroxypropyl methylcellulose | 0.8 kg |
| Water purified | 15.7 kg |
| Seeds for layering | |
| Non-pareil cores | 11.0 kg |

The active substance was suspended in a solution prepared of the hydroxypropyl methylcellulose in the water, and thereafter homogenized in a ball mill.

The suspension was sprayed onto the seeds in a Wurster equipped fluidized bed apparatus.

| Separating layer | |
| --- | --- |
| Core material (acc. to above) | 16.0 kg |
| Hydroxypropyl cellulose | 1.6 kg |
| Talc | 2.7 kg |
| Magnesium Stearate | 0.2 kg |
| Water purified | 32 kg |

The talc and magnesium stearate were suspended in a solution prepared by dissolving the hydroxypropyl cellulose in the water. The suspension was sprayed onto the core material in the same equipment as above.

| Enteric coating layer | |
|---|---|
| Prepared Pellets (acc. to above) | 20 kg |
| Methacrylic acid copolymer (30% dispersion) | 33 kg |
| Triethyl citrate | 3 kg |
| Mono- and diglycerides (NF) | 0.5 kg |
| Polysorbate 80 | 0.05 kg |
| Water purified | 20.5 kg |

The methacrylic acid copolymer dispersion was mixed with 1.0 kg of water and the triethylcitrate during agitation. (=Dispersion A.)

The polysorbate 80 was mixed with 19.5 kg of water, whereafter the mono- and diglycerides was added and this mixture was heated to above 70° C. for 10 minutes and the cooled during agitation to room temperature. (=Emulsion B.)

The emulsion B was added to suspension A and mixed to homogeneity.

The suspension (during agitation with a magnetic stirrer) was sprayed onto the core material in a Wurster equipped fluidized bed apparatus.

Directly after the enteric coating dispersion was applied, the pellets in the fluidized bed were sprayed with a hydroxypropyl methylcellulose solution containing magnesium stearate dispersed therein to accomplish an overcoating layer.

The composition of the dispersion was;

| Water purified | 8.0 kg |
|---|---|
| Hydroxypropyl methylcellulose | 0.4 kg |
| Magnesium stearate | 0.01 kg |

The obtained (overcoated) enteric coated pellets were mixed with powders and effervescent granules and thereafter compressed to effevescent tablets.

| Effervescent granules; | |
|---|---|
| Citric acid anhydrous | 11.4 kg |
| Sodium bicarbonate | 8.4 kg |
| Polyvinylpyrrolidone K-25 (PVP K-25) | 0.3 kg |
| EtOH 99% (w/v) | 0.8 kg |
| water purified | 0.3 kg |

The PVP K-25 was dissolved in the ethanol+water to give the granulating solution. This solution was used to granulate the citric acid sodium bicarbonate mixture. The wet mass was dried at 55° C. and after cooling to room temperature the granulate was milled to pass sieve 1.1 mm.

A pre-mix (for 400 tablets) was prepared by dry mixing in a Kenwood mixer the following;

| Sodium carbonate anhydrous | 38 g |
|---|---|
| Sorbitol | 160 g |
| Antifoam M | 5.8 g |

The premix was passed through a 0.5 mm sieve.

Final mixing (for 400 tablets) was performed in the same Kenwood mixer where the following ingredients were dry mixed:

| Effervescent granules from above | 910 g |
|---|---|
| Premix from above | 204 g |
| Sodium sterylfumarate (passing sieve 0.5 mm) | 7 g |
| Enteric coated pellets from above | 128 g |

Compression to tablets was done on a tableting machine equipped with punches giving 25 mm diameter flat tablets.

Tablet weight was 3120 mg. The compressed tablets hade an average height of 4.6 mm (n=4) and an average hardness of 67 N (n=10). The effervesense time of the tablets was measured by putting the tablet in a basket of metal wiring and then immersing the basket in 150 ml of water (20 degrees Celsius). The effervesense time was considered finished when there was no material left in the immersed basket. For this tablet composition the time was 55 seconds.

The pH of the obtained dispersion when testing the tablet in 150 ml purified water was 5.0. Gastric juice resistance (determined as % of the dose omeprazole remaining after exposure for 0.1 M HCL during 2 hours) was 94%.

EXAMPLE 5

Effervescent tablets containing 60 mg omeprazole.

Manufacturing of pellets.

| Core material | |
|---|---|
| Suspension for layering | |
| Magnesium omeprazole | 5.5 kg |
| Hydroxypropyl methylcellulose | 0.8 kg |
| Water purified | 15.7 kg |
| Seeds for layering | |
| Non-pareil cores | 11.0 kg |

The active substance was suspended in a solution prepared of the hydroxypropyl methylcellulose in the water, and thereafter homogenized in a ball mill.

The suspension was sprayed onto the seeds in a Wurster equipped fluidized bed apparatus.

| Separating layer | |
|---|---|
| Core material (acc. to above) | 16 kg |
| Hydroxypropyl cellulose | 1.6 kg |
| Talc | 2.7 kg |
| Magnesium Stearate | 0.2 kg |
| Water purified | 32 kg |

The talc and magnesium stearate were suspended in a solution prepared by dissolving the hydroxypropyl cellulose in the water. The suspension was sprayed onto the core material in the same equipment as above.

| Enteric coating layer | |
|---|---|
| Prepared pellets (acc. to above) | 20 kg |
| Methacrylic acid copolymer (30% dispersion) | 33 kg |
| Triethyl citrate | 3 kg |
| Mono- and diglycerides (NF) | 0.5 kg |
| Polysorbate 80 | 0.05 kg |
| Water purified | 20.5 kg |

The methacrylic acid copolymer dispersion was mixed with 1.0 kg of water and the triethylcitrate during agitation. (=Dispersion A.)

The polysorbate 80 was mixed with 19.5 kg of water, whereafter the mono- and diglycerides was added and this mixture was heated to above 70° C. for 10 minutes and the cooled during agitation to room temperature. (=Emulsion B.)

The emulsion B was added to suspension A and mixed to homogeneity.

The suspension (during agitation with a magnetic stirrer) was sprayed onto the core material in a Wurster equipped fluidized bed apparatus.

Directly after the enteric coating dispersion was applied, the pellets in the fluidized bed were sprayed with a hydroxypropyl methylcellulose solution containing magnesium stearate dispersed therein to accomplish an overcoating layer.

The composition of the dispersion was;

| Water purified | 8 kg |
|---|---|
| Hydroxypropyl methylcellulose | 0.4 kg |
| Magnesium stearate | 0.01 kg |

The obtained (overcoated) enteric coated pellets were mixed with powders and effervescent granules and thereafter compressed to effevescent tablets.

| Effervescent granules | |
|---|---|
| Citric acid anhydrous | 11.4 kg |
| Sodium bicarbonate | 8.4 kg |
| Polyvinylpyrrolidone K-25 (PVP K-25) | 0.3 kg |
| EtOH 99% (w/v) | 0.8 kg |
| water purified | 0.3 kg |

The PVP K-25 was dissolved in the ethanol+water to give the granulating solution. This solution was used to granulate the citric acid sodium bicarbonate mixture. The wet mass was dried at 55° C. and after cooling to room temperature the granulate was milled to pass sieve 1.1 mm.

A premix (for 400 tablets) was prepared by dry mixing in a Kenwood mixer the following;

| Sodium carbonate anhydrous | 38 g |
|---|---|
| Sorbitol | 160 g |
| Antifoam M | 5.8 g |

The premix was passed through a 0.5 mm sieve.

Final mixing (for 400 tablets) was performed in the same Kenwood mixer where the following ingredients were dry mixed:

| Effervescent granules from above | 910 g |
|---|---|
| Premix from above | 204 g |
| Sodium sterylfumarate (passing sieve 0.5 mm) | 7 g |
| Enteric coated pellets from above | 191 g |

Compression to tablets was done on a tableting machine equipped with punches giving 25 mm diameter flat tablets.

Tablet weight was 3230 mg. The compressed tablets hade an average height of 4.9 mm (n=4) and an average hardness of 51 N (n=10). The effervescense time of the tablets was measured by putting the tablet in a basket of metal wiring and then immersing the basket in 150 ml of water (20 degrees Celsius). The effervescense time was considered finished when there was no material left in the immersed basket. For this tablet composition the time was 58 seconds.

The pH of the obtained dispersion when testing a tablet in 150 ml purified water was 5.0. Gastric juice resistance (determined as % of the dose omeprazole remaining after exposure for 0.1 M HCl during 2 hours) was 94%.

EXAMPLE 6

Effervescent tablets containing 20 mg S-omeprazole magnesium Salt.

Manufacturing of pellets.

| Core material | |
|---|---|
| Suspension for layering | |
| S-omeprazole magnesium micronized. | 300 g |
| Hydroxypropyl methylcellulose | 75 g |
| Water purified | 1425 g |
| Seeds for layering | |
| Non-pareil cores | 300 g |

The active substance was suspended in a solution prepared of the hydroxypropyl methylcellulose in the water. The suspension was sprayed onto the seeds in a Wurster equipped fluidized bed apparatus.

| Separating layer | |
|---|---|
| Core material (acc. to above) | 294 g |
| Hydroxypropyl cellulose | 29 g |
| Talc | 50 g |
| Magnesium Stearate | 4 g |
| Water purified | 588 g |

The talc and magnesium stearate were suspended in a solution prepared by dissolving the hydroxypropyl cellulose in the water. The suspension was sprayed onto the core material in the same equipment as above.

| Enteric coating layer | |
| --- | --- |
| Prepared pellets (acc. to above) | 300 g |
| Methacrylic acid copolymer (30% dispersion) | 400 g |
| Triethyl citrate | 36 g |
| Mono- and diglycerides (NF) | 6 g |
| Polysorbate 80 | 0.6 g |
| Water purified | 235 g |

The methacrylic acid copolymer dispersion was mixed with the triethylcitrate during agitation. (=Dispersion A.)

The polysorbate 80 and the mono-and diglycerides were mixed with the water, whereafter this mixture was heated to above 70° C. for 10 minutes and emulsified in a mixer. Then it was cooled during agitation to room temperature. (=Emulsion B.)

The emulsion B was added to Dispersion A and mixed to homogeneity.

The obtained dipersion was sprayed onto the core material in a Wurster equipped fluidized bed apparatus.

Directly after the enteric coating dispersion was applied, the pellets in the fluidized bed were sprayed with a hydroxypropyl methylcellulose solution containing magnesium stearate dispersed therein to accomplish an overcoating layer. The composition of this dispersion was;

| Water purified | 120 g |
| --- | --- |
| Hydroxypropyl methylcellulose | 6 g |
| Magnesium stearate | 0.3 g |

Preparation of Effervescent Tablets.

The obtained (overcoated) enteric coated pellets were mixed with powders and effervescent granules and thereafter compressed to effevescent tablets.

| Effervescent granules | |
| --- | --- |
| Citric acid anhydrous | 11.4 kg |
| Sodium bicarbonate | 8.4 kg |
| Polyvinylpyrrolidone K-25 (PVP K-25) | 0.3 kg |
| EtOH 99% (w/v) | 0.8 kg |
| water purified | 0.3 kg |

The PVP K-25 was dissolved in the ethanol+water to give the granulating solution. This solution was used to granulate the citric acid sodium bicarbonate mixture. The wet mass was dried at 55° C. and after cooling to room temperature the granulate was milled to pass sieve 1.1 mm.

A pre-mix (for 50 tablets) was prepared by dry mixing in a mixer the following;

| Sodium carbonate anhydrous | 4.8 g |
| --- | --- |
| Sorbitol | 20 g |
| Antifoam M | 0.7 g |

The premix was passed through a 0.5 mm sieve.

Final mixing (for 50 tablets) was performed in the same mixer where the following ingredients were dry mixed:

| Effervescent granules from above | 114 g |
| --- | --- |
| Premix from above | 25.5 g |
| Sodium sterylfumarate (passing sieve 0.5 mm) | 0.9 g |
| Enteric coated pellets from above | 4.7 g |

Compression to tablets was done on a tableting machine equipped with punches giving 25 mm diameter flat tablets.

Tablet weight was 2890 mg. The compressed tablets hade an average height of 4.2 mm (n=4) and an average hardness of 100 N (n=5). The effervescense time of the tablets were measured by putting the tablet in a basket of metal wiring and then immersing the basket in 150 ml of water (20 degrees Celsius). The effervescense time was considered finished when there was no material left in the immersed basket. For this tablet composition the time was 55 seconds.

The pH of the obtained dispersion when testing in a tablet in 150 ml purified water was 5.0.

Gastric juice resistance (determined as % of the dose S-omeprazole remaining after exposure for 0.1 M HCl during 2 hours) was 94%.

The enteric coating layered pellets comprising a proton pump inhibitor may also be prepared as described in the following examples.

EXAMPLE 7

Preparation of enteric coating layered pellets by extrusion/spheronization.

| Core material | |
| --- | --- |
| Magnesium omeprazole | 600 g |
| Mannitol | 1000 g |
| Microcrystalline cellulose | 300 g |
| Hydroxypropyl cellulose | 100 g |
| Sodium lauryl sulphate | 6 g |
| Water purified | 802 g |
| Separating layer | |
| Core material (acc. to above) | 400 g |
| Hydroxypropyl methylcellulose | 48 g |
| Water purified | 960 g |
| Enteric coating layer | |
| Pellets covered with separating layer (acc. to above) | 200 g |
| Methacrylic acid copolymer | 100 g |
| Triethyl citrate | 30 g |
| Mono- and diglycerides (NF) | 5 g |
| Polysorbate 80 | 0.5 g |
| Water purified | 309 g |

Sodium lauryl sulphate is dissolved in purified water to form the granulation liquid. Magnesium omeprazole, mannitol, microcrystalline cellulose and hydroxypropyl cellulose are dry-mixed. The granulation liquid is added to the powder mixture and the mass is wet-mixed.

The wet mass is forced through an extruder equipped with screens of size 0.5 mm. The extrudate is spheronized on a friction plate in a spheronizing apparatus. The core material is dried in a fluid bed dryer and classified. The prepared core material is covered by a separating layer in a fluid bed apparatus with a hydroxypropyl methylcellulose/water solution.

The enteric coating layer is applied to the pellets covered with separating layer from an aqueous dispersion of methacrylic acid copolymer plasticized with triethyl citrate to which a mono- and diglycerides/polysorbate dispersion has been added. The pellets are dried in a fluid bed apparatus.

EXAMPLE 8

Preparation of enteric coating layered pellets by powder layering of sugar sphere seeds.

| Core material | |
| --- | --- |
| Magnesium omeprazole | 1500 g |
| Sugar sphere seeds | 1500 g |
| Hydroxypropyl methylcellulose | 420 g |
| Aerosil ® | 8 g |
| Water purified | 4230 g |
| Separating layer | |
| Core material (acc. to above) | 500 g |
| Hydroxypropyl cellulose | 40 g |
| Talc | 67 g |
| Magnesium stearate | 6 g |
| Water purified | 800 g |
| Enteric coating layer | |
| Pellets covered with separating layer (acc. to above) | 500 g |
| Methacrylic acid copolymer | 200 g |
| Triethyl citrate | 60 g |
| Water purified | 392 g |

Magnesium omeprazole, part of the hydroxypropyl methylcellulose and Aerosil® are dry-mixed forming a powder. Sugar sphere seeds (0.25–0.40 mm) are layered with the powder in a centrifugal fluidized coating granulator while spraying a hydroxypropyl methylcellulose solution (6%, w/w).

The prepared core material is dried and covered by a separating layer in a centrifugal fluidized coating-granulator. A fluid bed apparatus is used for enteric coating layering.

EXAMPLE 9

Preparation of enteric coating layered pellets with silicon dioxide seeds.

| Core material | |
| --- | --- |
| Magnesium omeprazole | 8.0 kg |
| Silicon dioxide | 8.0 kg |
| Hydroxypropyl methylcellulose | 1.4 kg |
| Sodium lauryl sulphate | 0.1 kg |
| Water purified | 28.0 kg |
| Separating layer | |
| Core material (acc. to above) | 10.0 kg |
| Hydroxypropyl methylcellulose | 0.8 kg |
| Water purified | 10.0 kg |
| Enteric coating layer | |
| Pellets covered with separating layer (acc. to above) | 300 g |
| Methacrylic acid copolymer | 124 g |
| Polyethylene glycol 400 | 25 g |
| Mono- and diglycerides (NF) | 3 g |
| Polysorbate 80 | 1 g |
| Water purified | 463 g |

Suspension layering is performed in a fluid bed apparatus. Magnesium omeprazole is sprayed onto the silicon dioxide seeds from a water suspension containing the dissolved binder and a surface active ingredient.

The prepared core material is covered with a separating layer in a fluid bed apparatus with a hydroxypropyl methylcellulose solution. The enteric coating layer consisting of methacrylic acid copolymer, mono- and diglycerides, polyethylene glycol 400 and polysorbate is sprayed onto the pellets covered with separating layer in a fluid bed apparatus.

EXAMPLE 10

Preparation of enteric coating layered pellets.

| Enteric coating layer | |
| --- | --- |
| Pellets covered with separating layer (manufacturing and composition as in example 2) | 500 g |
| Methacrylic acid copolymer | 250 g |
| Polyethylene glycol 6000 | 75 g |
| Mono- and diglycerides (NF) | 12.5 g |
| Polysorbate 80 | 1.2 g |
| Water purified | 490 g |

EXAMPLE 11

Preparation of enteric coating layered pellets.

| Enteric coating | |
| --- | --- |
| Pellets covered with separating layer (manufacturing and composition as in example 1) | 500 g |
| Hydroxypropyl methylcellulose phthalate | 250 g |
| Cetanol | 50 g |
| Ethanol (95%) | 1000 g |
| Acetone | 2500 g |

EXAMPLE 12

Preparation of enteric coating layered pellets.

| Core material | |
| --- | --- |
| Omeprazole | 225 g |
| Mannitol | 1425 g |
| Hydroxypropyl cellulose | 60 g |
| Microcrystalline cellulose | 40 g |
| Lactose anhydrous | 80 g |
| Sodium lauryl sulphate | 5 g |
| Disodium hydrogen phosphate dihydrate | 8 g |
| Water purified | 350 g |
| Separating layer | |
| Core material (acc. to above) | 300 g |
| Hydroxypropyl cellulose | 30 g |
| Talc | 51 g |
| Magnesium stearate | 4 g |
| Enteric coating layer | |
| Pellets covered with separating layer (acc. to above) | 300 g |
| Methacrylate acid copolymer | 140 g |
| Triethyl citrate | 42 g |
| Mono- and diglycerides (NF) | 7 g |
| Polysorbate 80 | 0.7 g |

The dry ingredients for producing the core material are well mixed in a mixer. Addition of granulation liquid is made and the mixture is kneaded and granulated to a proper consistency. The wet mass is pressed through an extruder screen and the granules are converted into a spherical form in a spheronizer. The core material is dried in a fluid bed apparatus and classified into a suitable particle size range, e.g. 0.5–1.0 mm. The prepared core material is covered with a separating layer and is enteric coating layered as described in previous examples.

Preparation of active substance.

Magnesium omeprazole used in some of the examples is produced according to the process described in WO95/01977, the single enantiomers of omeprazole salts are prepared as described in WO94/27988 and omeprazole is produced according to the process disclosed in EP-A1 0005129. These documents are hereby incorporated in a whole by reference.

What is claimed is:

1. An oral pharmaceutical composition in the form of a multiple unit effervescent tablet comprising, as a first component, a core material comprising an acid susceptible proton pump inhibitor, and as a separate second component, at least one effervescent tablet constituent, wherein the core material is in the form of pellets covered with an enteric coating layer having mechanical properties such that the acid resistance of the enteric coated pellets is not significantly affected by compression of the pellets with the other tablet components during tableting.

2. A process for the manufacture of a composition in the form of a tableted multiple unit effervescent dosage form comprising, as a first component, a core material comprising an acid susceptible proton pump inhibitor, and as a second component, at least one effervescent tablet constituent, wherein the process comprises the steps of:

(a) preparing the core material in the form of enteric coating layered pellets;

(b) mixing the enteric coating layered pellets with the second component; and (c) compressing the dry mixture into a multiple unit effervescent tablet without affecting any significant change of the acid resistance of the enteric coating layered pellets.

3. The composition according to claim 1, wherein the proton pump inhibitor is one of the following compounds

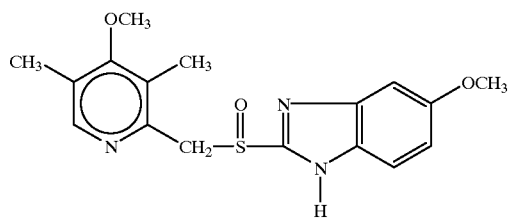

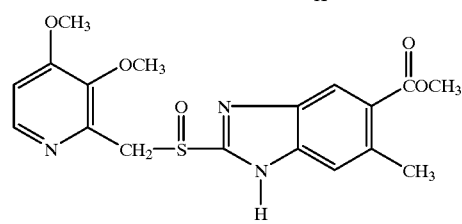

-continued

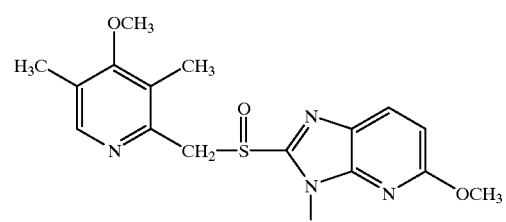

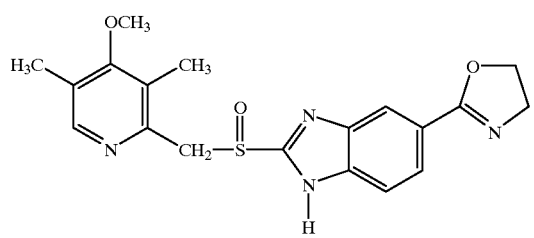

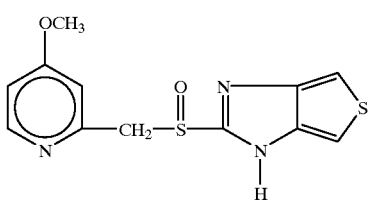

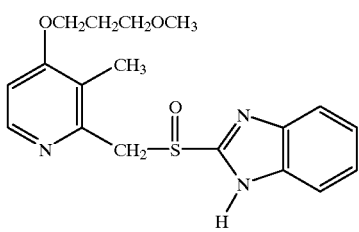

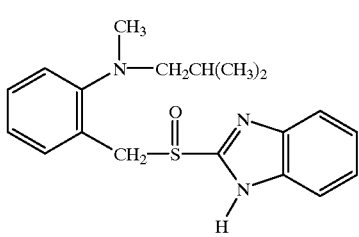

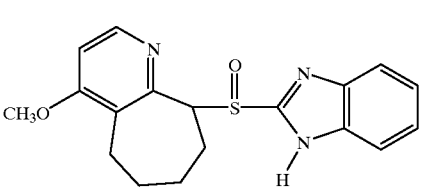

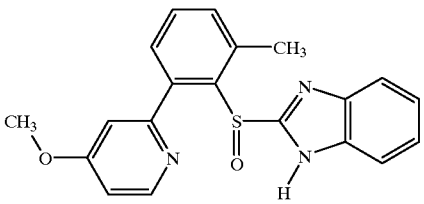

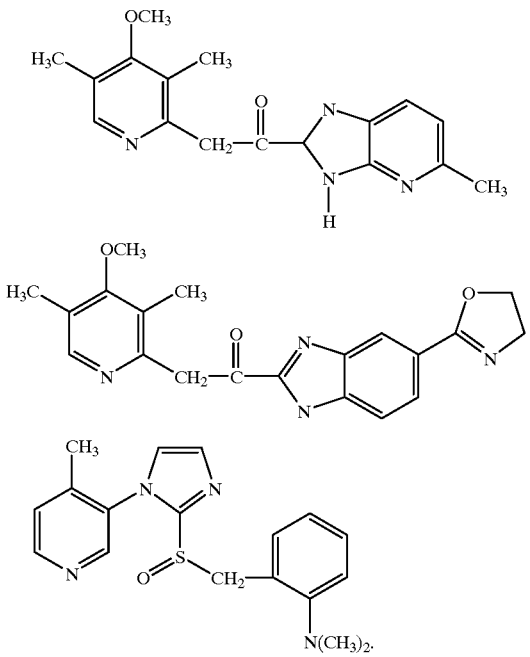

4. The composition according to claim 1, wherein the proton pump inhibitor is omeprazole, an alkaline salt of omeprazole, S-omeprazole or an alkaline salt of S-omeprazole.

5. The composition according to claim 1, wherein the acid resistance of the enteric coating layered pellets is in compliance with the requirements on enteric coated articles defined in the United States Pharmacopeia USP.

6. The composition according to claim 1, wherein the acid resistance of the enteric coating layered pellets does not decrease more than 10% upon tableting of the pellets into the tableted multiple unit effervescent dosage form.

7. The composition according to claim 1, wherein the enteric coating comprises a plasticizer.

8. The composition according to claim 1, wherein the enteric coating layer comprises a water-based polymer system.

9. The composition according to claim 1, wherein the enteric coating layer has a thickness of at least 10 μm.

10. The composition according to claim 1, wherein the enteric coating layered pellets are further covered with an overcoat layer comprising a film-forming agent.

11. The composition according to claim 1, wherein the second component comprises a carbon dioxide source and a solid acidic compound.

12. The composition according to claim 1, wherein the second component comprises sodium carbonate, sodium bicarbonate and solid citric acid.

13. The composition according to claim 1 wherein the proton pump inhibitor is a compound of the general formula I, an alkaline salt of the compound, a single enantiomer of the compound or an alkaline salt of the single enantiomer

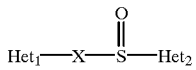

I wherein

Het$_1$ is

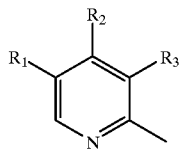 or 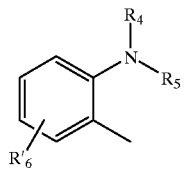

Het$_2$ is

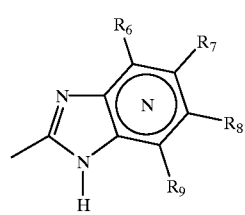 or

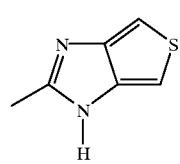 or 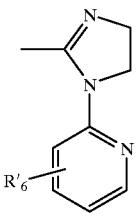

X =

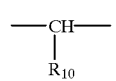 or 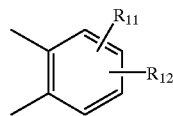

wherein
  N in the benzimidazole moiety means that one of the carbon atoms substituted by of $R_6$–$R_9$ optionally may be exchanged for a nitrogen atom without any substituents;
  $R_1$, $R_2$ and $R_3$ are the same or different and are selected from the group consisting of hydrogen, alkyl, alkoxy, alkoxy substituted by fluorine, alkylthio, alkoxyalkoxy, dialkylamino, piperidino, morpholino, halogen, phenyl and phenylalkoxy;
  $R_4$ and $R_4$ are the same or different and are selected from the group consisting of hydrogen, alkyl and arylalkyl;
  $R'_6$ is hydrogen, halogen, trifluoromethyl, alkyl or alkoxy;
  $R_6$–$R_9$ are the same or different and are selected from the group consisting of hydrogen, alkyl, alkoxy, halogen, haloalkoxy, alkylcarbonyl, alkoxycarbonyl, oxazolinyl and trifluoroalkyl, or adjacent groups $R_6$–$R_9$ form ring structures;
  $R_{10}$ is hydrogen or forms an alkylene chain together with $R_3$; and
  $R_{11}$ and $R_{12}$ are the same or different and are selected from the group consisting of hydrogen, halogen, alkyl and alkyl groups, alkoxy groups and moieties thereof which are branched or straight $C_1$–$C_9$-chains or cyclic alkyl groups.

14. The composition according to claim 1, wherein the core material further comprises a pharmaceutically acceptable additive selected from the group consisting of binders, surfactants, fillers, disintegrating agents, alkaline reacting compounds and mixtures thereof.

15. The composition according to claim 1, wherein the core material is covered by a separating layer located between the core material and the enteric coating layer.

16. The composition according to claim 1, wherein the inert seeds are soluble sugar seeds.

17. The composition according to claim 1, wherein the proton pump inhibitor is in the form of homogeneous cores.

18. The composition according to claim 15, wherein the separating layer comprises a material selected from the group consisting of (a) polymeric, film-forming compounds, (b) tablet excipients which are water soluble or disintegrate rapidly in water and (c) pH-buffering, alkaline compounds.

19. The composition according to claim 1, wherein a coating layer comprising the proton pump inhibitor, optionally in admixture with pharmaceutically acceptable additives, is in the form of a layer on inert seeds.

20. A method for inhibiting gastric acid secretion in mammals and man which comprises administering to a host in need thereof a therapeutically effective dose of a tableted multiple unit effervescent dosage form according to claim 1.

21. A method for the treatment of gastrointestinal inflammatory diseases in mammals and man which comprises administering to a host in need thereof a therapeutically effective dose of a tableted multiple unit effervescent dosage form according claim 1.

22. The composition according to claim 19, wherein the inert seeds have a size of 0.1–2 mm.

23. The process according to claim 2, wherein the core material further comprises a pharmaceutically acceptable additive selected from the group consisting of binders, surfactants, fillers, disintegrating agents, alkaline reacting compounds and mixtures thereof.

24. The process according to claim 2, which further comprises covering the core material with at least one separating layer before applying the enteric coating layer.

25. The process according to claim 2 or 24, which further comprises covering the enteric coating layered pellets with an overcoating layer before the pellets are mixed with the second component and compressed into the tableted dosage form.

26. The composition according to claim 13, wherein the cyclic alkyl groups of $R_{11}$ and $R_{12}$ are cycloalkylalkyl.

27. The composition according to claim 10, wherein the overcoating comprises pharmaceutically acceptable excipients.

* * * * *

UNITED STATES PATENT AND TRADEMARK OFFICE
CERTIFICATE OF CORRECTION

PATENT NO. : 6,132,770
DATED : October 17, 2000
INVENTOR(S) : Per Johan Lundberg Page 1 of 1

It is certified that error appears in the above-identified patent and that said Letters Patent is hereby corrected as shown below:

<u>Column 28, claim 13,</u>
Line 38, delete "of".
Line 46, delete the second instance of "$R_4$" and substitute therefor -- $R_5$ --.

<u>Column 29, claim 16,</u>
Line 1, delete "claim 1" and substitute therefor -- claim 19 --.

Signed and Sealed this

Fourth Day of December, 2001

Attest:

NICHOLAS P. GODICI
*Attesting Officer*   *Acting Director of the United States Patent and Trademark Office*

UNITED STATES PATENT AND TRADEMARK OFFICE
CERTIFICATE OF CORRECTION

PATENT NO. : 6,132,770
DATED : October 17, 2000
INVENTOR(S) : Per Johan Lundberg Page 1 of 2

It is certified that error appears in the above-identified patent and that said Letters Patent is hereby corrected as shown below:

Column 6,
Lines 40-50, delete the chemical structure and substitute the following structure therefor:

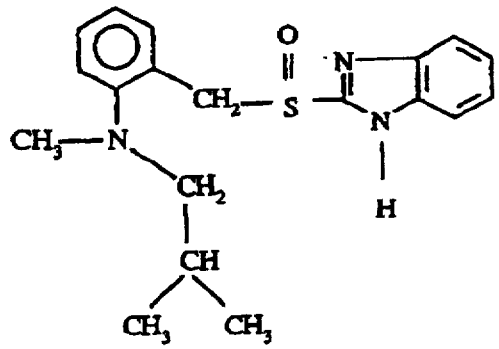

UNITED STATES PATENT AND TRADEMARK OFFICE
CERTIFICATE OF CORRECTION

PATENT NO. : 6,132,770
DATED : October 17, 2000
INVENTOR(S) : Per Johan Lundberg It is certified that error appears in the above-identified patent and that said Letters Patent is hereby corrected as shown below:

Claim 3,
Add the following structures:

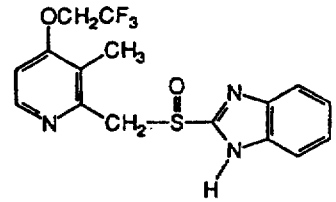

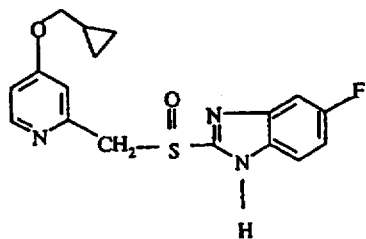

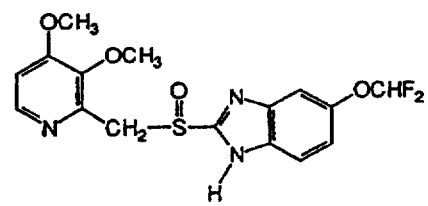

Column 27, claim 3,
Delete the first and second structures.

Signed and Sealed this

Fifth Day of February, 2002

Attest:

Attesting Officer

JAMES E. ROGAN
Director of the United States Patent and Trademark Office